United States Patent [19]

Martin

[11] 4,382,380
[45] May 10, 1983

[54] PLANT WATERING INDICATOR

[76] Inventor: Charles Martin, 11 Troon Ct., Greenhills, East Kilbride, Great Britain

[21] Appl. No.: 189,562

[22] Filed: Sep. 23, 1980

[30] Foreign Application Priority Data

Sep. 26, 1979 [GB] United Kingdom ............... 7933394

[51] Int. Cl.³ .................... G01N 33/18; G01N 33/24
[52] U.S. Cl. ........................................ 73/73; 116/206
[58] Field of Search ................... 73/73, 335; 116/206

[56] References Cited

U.S. PATENT DOCUMENTS

| | | | |
|---|---|---|---|
| 3,019,638 | 2/1962 | Klein | 73/73 |
| 3,824,844 | 7/1974 | Strickland | 73/73 |
| 3,951,098 | 4/1976 | Meyer | 116/206 |
| 4,130,012 | 12/1978 | Lockerby | 73/73 |
| 4,201,080 | 5/1980 | Slepak | 116/206 |

FOREIGN PATENT DOCUMENTS 2301013 9/1976 France ................................. 73/73

Primary Examiner—Charles A. Ruehl
Assistant Examiner—Denis E. Corr
Attorney, Agent, or Firm—Gerald J. Ferguson, Jr.; Joseph J. Baker

[57] ABSTRACT

A plant watering indicator device comprises an elongate member which is insertable into soil and which has a layer of hygroscopic material, calcium hydroxide, disposed thereon. At the end of the member not inserted into the soil there is a transparent plastic film, which is a different color from the member attached to the member and which covers the calcium hydroxide layer thereat. There is a gap in the calcium hydroxide layer disposed beneath the plastic film. In use the indicator is inserted into the soil and, if sufficient water is present, the water is attracted up between the film and the member and the calcium hydroxide changes from opaque to translucent whereby the color of the member is contrasted against the color of film above the gap, giving a visual indication of the water content of the plant.

12 Claims, 6 Drawing Figures

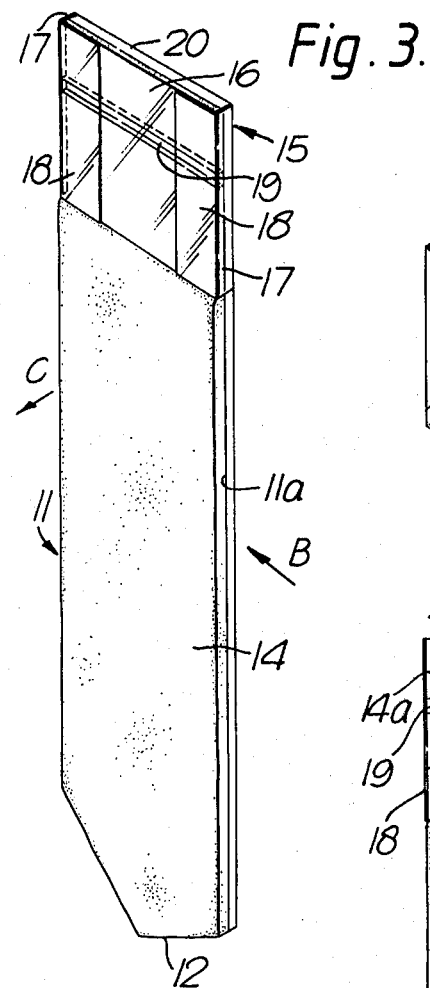
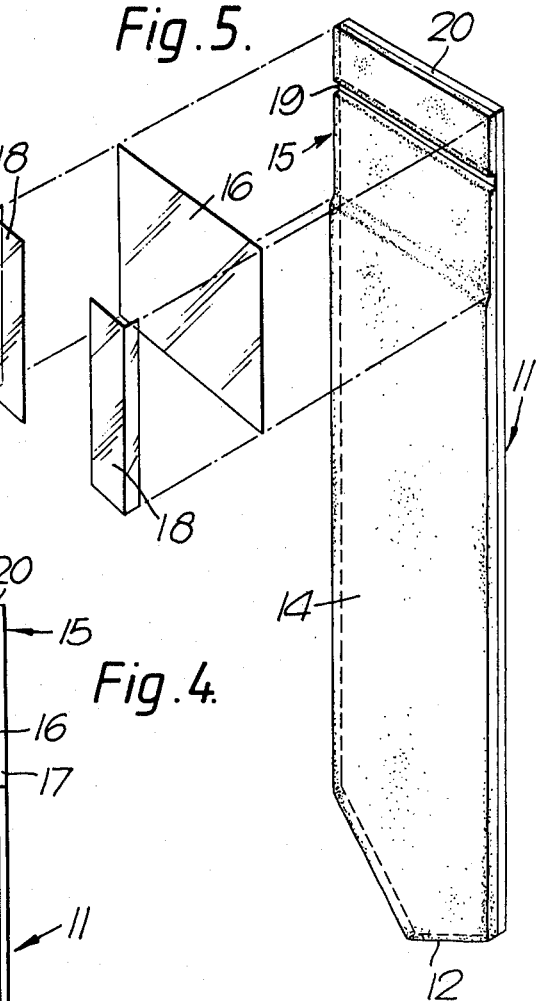
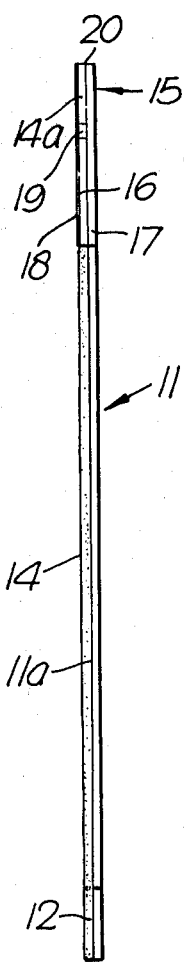

PLANT WATERING INDICATOR

The present invention relates to apparatus for indicating the presence or non-presence of moisture in soil especially, but not exclusively, in the soil of pot plants.

There is known in the art, apparatus for indicating the presence of moisture in soil in pot plants which operates on the principle of electrical resistance measurement. This apparatus usually comprises a probe containing an electrical sensor attached to an indicating means. When the probe is inserted into the soil, an electrical signal dependent on the electrical resistance of the soil is received by the indicating means, from the probe, which is indicative of the moisture content of the soil.

Such apparatus, however, has several disadvantages: an electrical power supply is required for the apparatus to operate; the components of such known apparatus require machining and intricate assembly resulting in the cost per unit being often higher than the cost of the plants; the device can only be used, in a practical sense for 'spot' measurements of soil moisture content and, if there are several plants, as is common in most offices and households, then the probe requires to be inserted into the soil of each plant, in turn.

Another known device comprises a piece of tissue paper 1 sandwiched between two layers 2a and 2b of transparent plastic forming an envelope, as shown in FIGS. 1, 2. The shape of the device is generally elongate having a pointed portion 3 for inserting into the soil. In the device near to the pointed portion there is located an aperture 4 which is elongate transverse to the shape of the device. There is located another large aperture 5 approximately halfway along the device and an aperture 6 near to the top 7 of the device. When the device is inserted into the soil both apertures 4 and 5 are located beneath the soil level. Water from the soil enters the apertures and is drawn up into the tissue paper 1 above the soil level 8 between the plastic layers 2a and 2b by a combination of a wick and capillary action. When the water is drawn into the tissue paper 1a above the soil the device changes from almost opaque to translucent which is indicative that the moisture, or water, content of the soil is satisfactory. Conversely, if no change occurs or if a change appears to be occuring very slowly then this is indicative that the plant requires to be watered. This device has the disadvantage that water can become trapped between the plastic layers which causes the tissue paper to rot, consequently the effectiveness of the device is reduced. Also, local entrapment of water can result in fungal growth between the plastic layers which affects the sensitivity of the device and which confuses the visual changes which occur.

Another disadvantage is that the aperture 5 is located at a specific level beneath this aperture consequently an artificially low level is produced resulting in an erroneous indication of when the plant requires to be watered. Additionally, due to the small size of the apertures, particularly aperture 4, they are easily and frequently blocked by particles of grit and matter in the soil which considerably reduce the effectiveness and usefulness of the indicator.

A further disadvantage is the poor visual contrast obtained, in practice, from the indicator between moist soil and dry soil which gives uncertainty and doubt as to when the plant actually requires to be watered.

An object of the present invention is to mitigate or obviate the disadvantages of these known devices.

According to the present invention there is provided apparatus for indicating when a plant requires to be watered comprising a member insertable into the soil, said member having a layer of hygroscopic material disposed thereon, said layer being covered, at least in part, by a light transmissive cover, and means for preventing evaporation of water from the layer beneath said cover.

An embodiment of the present invention will now be described by way of example with reference to the accompanying drawings in which:

FIG. 3 is a view of the apparatus according to the present invention;

FIG. 4 is a view of FIG. 2 taken in the direction B;

FIG. 5 is an exploded view of the apparatus shown in FIGS. 3 and 4 in the direction C;

Figure 6:
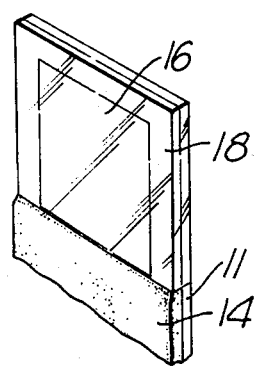
FIG. 6 is a modification of a view of a part of the apparatus of FIGS. 3-5 in accordance with the present invention.

Referring now to FIGS. 3-6, an elongate member 11 of a particular colour has a pointed end 12 adapted to be inserted into the soil of a pot plant. A layer of paint (not shown) or similar substance with adhesive properties is first applied to the face 11a of the member 11. A layer of hygroscopic material, such as calcium hydroxide, is then disposed on top of the paint forming a substrate 14. The hygroscopic material can also be mixed with a material with adhesive properties in various ratios to provide a suitable coating medium. At the end 15 of the member 11, a transparent coloured cover 16, which may be, for example, a plastic film, is mounted on the member 11 at the edges 17, conveniently by moisture impermeable adhesive tape 18 providing a competent moisture seal thereat. The substrate disposed beneath the plastic film 16 forms a thinner layer 14a than the layer outwith the film 16. The film 16 is a different colour from the member 11. The substrate 14 on the member 11 has a discontinuity 19 beneath the film 16 which may, conveniently, be produced by scratching off some calcium hydroxide from the member 11. Alternatively, the discontinuity 19 may be a groove in the plastic member 11 or a non-hygroscopic material. The discontinuity 19 is near and substantially parallel to, the top edge 20 of the member 11.

In use, the member 11 is inserted by its pointed end 12 into the soil. The calcium hydroxide layer absorbs moisture from the soil, if present, and in the process appears to turn from a milky-white colour, when anhydrous, which is opaque, to essentially no colour, which is translucent, and through which the colour of the elongate member 11 is seen. The moisture rises up the layer 14 and then between the cover 16 and the layer 14 more rapidly by capillary action causing the layer of material to appear translucent in the process, thus enabling the colour of the member 11 to be viewed through the film 16. The substrate appears to change colour relative to the edges of the film 16, although in fact, this is due to the colour of the member showing through. Thus this provides a visual indication that moisture is present in the soil being tested. The higher and faster the colour change occurs, the greater the moisture or water content of the soil. The discontinuity 19 presents a barrier to the movement of moisture by capillary action and consequently the moisture cannot flow up between the substrate 14 and the cover 16 and evaporate to the atmosphere. Alternatively, evaporation of moisture from the substrate 14 is also prevented when the film 16 (FIG. 6) is sealed to the elongate member 11 by adhesive tape 18, or the like at its top end 11b. Thus this apparatus prevents erroneous indications of soil which is dry or has a low moisture content.

Figure 1:
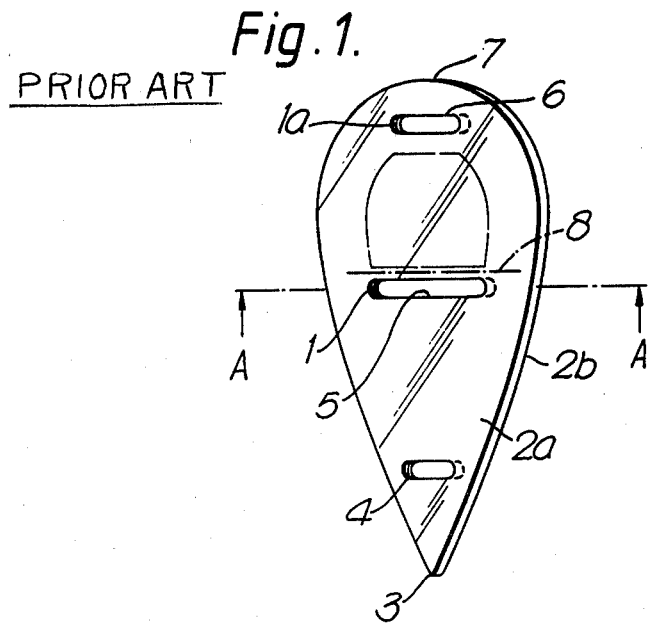
FIG. 1 is a view of a plant watering indicator known in the art.
Figure 2:
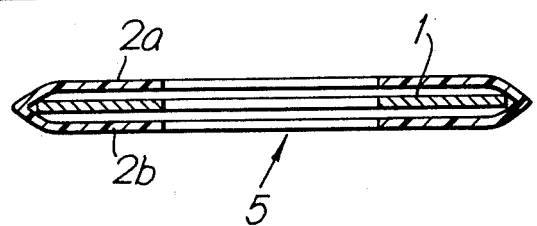
FIG. 2 is a sectional view of part of the indicator of FIG. 1 taken along the direction A—A.

Without departing from the scope of the invention it will readily be understood that several modifications can be made to parts of the apparatus shown in FIGS. 2-6. For example, the elongate member 11 may be circular in cross-section or of any other cross-section; a coating of the hygroscopic material may be applied longitudinally to part or all of the perimeter of the elongate member, and the light transmissive cover may be of any suitable material such as glass. Furthermore, the apparatus could readily be incorporated into a plant pot wall, a transparent window being provided in the wall through which the change in colour due to soil moisture content could be observed.

In addition, many other hygroscopic materials could be used for example calcium chloride, sodium sulphate, magnesium hydroxide, calcium carbonate alumena, polyethylene oxide and polyurethane oxide amongst chemical compounds, and non-chemical hygroscopic substances such as tissue paper, cotton, woven textiles and the like, the only requirement being that the hygroscopic material should not dissolve in the water.

An advantage of the apparatus according to the present invention described in the embodiment, is that when the moisture in the soil is used up by the plant, the calcium hydroxide layer dries out and in the process returns to its original anhydrous milky-white and opaque colour, thus each indicating device is reconstitutable and reusable. Further advantages are; few simple and cheap materials are used which provide a low cost per unit enabling each plant to have a device permanently inserted into its soil providing a continuous indication of the moisture content of the soil, and visual indication of the watering requirements of each plant, even in a group of plants, is provided at a glance.

The use of the adhesive beneath the layer of hygroscopic material provides a good bond for the hygroscopic substrate; and adhesion of the substrate is relatively unaffected by flexion of the member, otherwise flaking of the substrate may occur which would render the indicator less effective.

A further advantage is that, at the discontinuity which presents a barrier to the capillary movement of moisture, there is a clearer visual indication of the presence or non-presence of moisture since there is a distinct colour difference between the dry substrate above the groove and the wet substrate below the groove.

Thus there is provided a plant watering indicator which is effective, efficient and reliable, uses simple and easily available materials and is economic to produce.

I claim:

1. Apparatus for indicating when a plant requires to be watered comprising, a member insertable into the soil, said member having a layer of hygroscopic material disposed thereon wherein said hygroscopic material is mixed in a mixture with a material having adhesive properties, said mixture retaining the hygroscopic properties of said hygroscopic material, said layer being covered at least in part by a light transmissive cover, and said layer having a discontinuity therein for preventing evaporation of water from the layer located beneath said cover.

2. Apparatus as claimed in claim 1 wherein said cover is a transparent plastic.

3. Apparatus as claimed in either claim 1 or claim 2 wherein said colour of the cover and the colour of the member are different.

4. Apparatus as claimed in any one of claims 1 or 2 wherein the member is elongate and substantially rectangular in transverse cross-section.

5. Apparatus as claimed in claim 3 wherein the member is elongate and substantially rectangular in transverse cross-section.

6. Apparatus for indicating when a plant requires to be watered comprising a member insertable into the soil, said member having a layer of hygroscopic material consisting of calcium hydroxide disposed thereon, the layer of calcium hydroxide being covered by a transparent plastic cover, said layer having a discontinuity therein for preventing the evaporation of water from the layer located beneath the cover and the colour of the cover and the member being different, and wherein the said hygroscopic material is mixed in a mixture with a material having adhesive properties, said mixture retaining the hygroscopic properties of said hygroscopic material.

7. Apparatus for indicating when a plant requires to be watered comprising a member insertable into the soil, said member having a layer of hygroscopic material selected from the group, calcium chloride, sodium sulphate, magnesium hydroxide, calcium carbonate, alumena, polyethylene oxide, polyurethane oxide, tissue paper, cotton and woven textiles disposed thereon, said layer of hygroscopic material being covered by a plastic transparent cover, and the colour of the cover and the member being different, and wherein said hygroscopic material is mixed in a mixture with a material having adhesive properties, said mixture retaining the hygroscopic properties of said hygroscopic material.

8. Apparatus as claimed in claim 6 or claim 7 wherein the member is elongate and substantially rectangular in transverse cross-section.

9. Apparatus as claimed in claim 6 or claim 7 wherein the member is elongate and substantially circular in transverse cross-section.

10. Apparatus for indicating when a plant requires to be watered comprising a plant container having a window located therein, a layer of hygroscopic material disposed on the window and on the surface of the plant container wall, a cover located over said window and the layer of material on the window, said layer having a discontinuity therein for preventing evaporation of water from the layer located beneath the cover, and wherein the said hygroscopic material is mixed in a mixture with a material having adhesive properties, said mixture retaining the hygroscopic properties of said hygroscopic material.

11. Apparatus as claimed in claim 10 wherein the cover is a transparent plastic, the colour of the cover and the plant container being different.

12. Apparatus as claimed in claim 10 or claim 11 wherein the hygroscopic material is selected from the group, calcium hydroxide, calcium diloride, sodium sulphate, magnesium hydroxide, calcium carbonate, alumena, polyethylene oxide, polyurethane oxide, tissue paper, cotton and woven textiles thereon.

* * * * *